United States Patent [19]

Bucourt et al.

[11] Patent Number: 5,795,884
[45] Date of Patent: Aug. 18, 1998

[54] 3-KETO-NOR-PREGNENES SUBSTITUTED IN THE 6-POSITION AND TREATMENT OF MENOPAUSE

[75] Inventors: Robert Bucourt; Alain Piasco, both of Nice; Claude Tchernatinsky, Beausoleil, all of France

[73] Assignee: Laboratoire Theramex SA, France

[21] Appl. No.: 643,623

[22] Filed: May 6, 1996

Related U.S. Application Data

[63] Continuation of Ser. No. 185,945, Feb. 15, 1994, abandoned.

[30] Foreign Application Priority Data

Jul. 18, 1991 [FR] France .................... 91 09097

[51] Int. Cl.[6] .................. A61K 31/56; C07J 5/00
[52] U.S. Cl. .................. 514/178; 552/539; 552/593
[58] Field of Search ................. 552/539, 593; 514/178

[56] References Cited

FOREIGN PATENT DOCUMENTS 2 148261  4/1972  Germany .

OTHER PUBLICATIONS

Dorai et al, J. Pharmacol. & Exper. Ther., pp. 620–625, 1991.
Gilbert et al, Steroids, vol. 23, No. 4., Apr. 1973 pp. 585–607.
CA 77: 48724, Anney, 1971.
CA 115: 175 131, Dorai et al, 1991.

*Primary Examiner*—Rebecca Cook
*Attorney, Agent, or Firm*—Bierman, Muserlian and Lucas

[57] ABSTRACT

A 3-keto-19-nor-pregnene of the formula

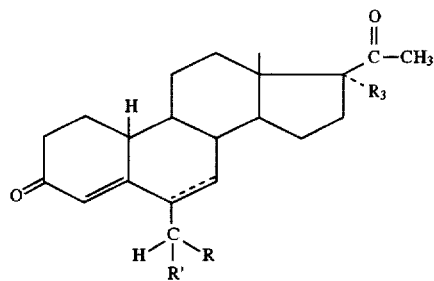

wherein R is selected from the group consisting of hydroxy, acyloxy of an organic carboxylic acid, lower alkoxy, halogen and lower alkyl, R' is selected from the group consisting of hydrogen and halogen, or R and R' together form oxygen, $R_3$ is selected from the group consisting of methyl, —OH and lower acyloxy of an organic carboxylic acid and the dotted line is an optional double bond in the 6,7-position useful for treating the symptoms of menopause in females.

7 Claims, No Drawings

3-KETO-NOR-PREGNENES SUBSTITUTED IN THE 6-POSITION AND TREATMENT OF MENOPAUSE

PRIOR APPLICATION

This application is a continuation of U.S. patent application Ser. No. 185,945 filed Feb. 15, 1994, now abandoned which claims the benefit of PCT application No. FR 92/00697 filed Jul. 17, 1992 claiming priority of French patent application Ser. No. 91/09097 filed Jul. 18, 1991.

The present invention relates to the domain of chemistry and more particularly to that of therapeutic chemistry.

A more particular subject of the invention is new steroid derivatives, substituted in position 6, as well as the processes for obtaining them.

A specific subject of the invention is 19-nor pregnanes substituted in position 6 chosen from the group constituted by:

the 3-keto Δ4- 19-nor pregnanes substituted in position 6 corresponding to partial formula (A)

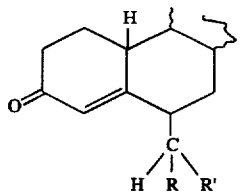

in which R represents a hydroxy, an acyloxy, an alkoxy, at halogen or a lower alkyl radical R' represents a hydrogen, a halogen or R and R' form together the oxygen of a carbonylated function and the 3-keto 19-nor Δ4,6-pregnadienes substituted in position 6 corresponding to partial formula (B)

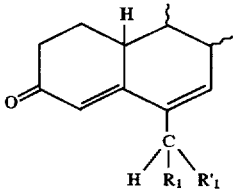

in which $R_1$ represents a hydrogen, a halogen, a hydroxyl, an alkoxy, an acyloxy or a lower alkyl $R'_1$ represents hydrogen or a halogen or $R_1$ and $R'_1$ form together the oxygen of a carbonylated function with the restriction that $R_1$ and $R'_1$ are not both hydrogen or a halogen atom.

In the two partial formulae A and B, the other rings of the steroid nucleus are not shown. They are those of a pregnane and can carry a side chain in position 17beta of acyl type having 2 to 8 carbon atoms or of hydroxyalkyl type having 2 to 8 carbon atoms or of acyloxy type having 2 to 8 carbon atoms. Position 17alpha can contain a hydrogen, a free, esterified or alkylated hydroxyl having 1 to 3 carbon atoms, a halogen or a saturated or unsaturated lower alkyl radical.

Position 16 can also carry a methyl, an ethyl, a methylene or be inserted in a carbon-carbon double bond with carbon 17 or carbon 15.

Position 11 can carry a hydroxyl, the oxygen of a ketone function or a methylene radical.

Among the compounds of partial formula A, there will be mentioned quite particularly the compounds for which

represents a formyl group, a hydroxymethyl group, an acyloxy methyl group, a dihalogenomethyl group or an alkoxymethyl group.

Among the compounds of partial formula B, those will be mentioned for which the group

represent's a hydroxy methyl, a methoxy methyl, a halogenomethyl, a formyl, a lower alkyl or a dialkoxymethyl.

There will be mentioned quite particularly amongst these compounds, the 19-nor pregna 4-ene 6-hydroxy methylated compounds which are the currently preferred compounds corresponding to partial formula (C)

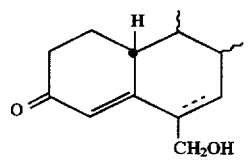

in which the dotted line symbolizes an optional double bond in position 6–7.

In the absence of a double bond, the hydroxymethyl group can be alpha or beta oriented.

These pregnanes can contain a hydroxyl or an alkyl in position 17alpha and a linear or branched oxoalkyl or hydroxyalkyl chain in position 17beta.

The invention also relates to the 6-methylenic derivatives of partial formula (D)

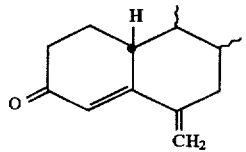

which have up to now been described as synthesis intermediates for 6-methylated 19-nor pregnanes (cf. British Patent 1,515,441).

The invention relates specifically, as new compounds, to the following derivatives;

3,20-dioxo 6-formyl 17alpha-acetoxy 19-nor pregna 4-ene 3,20-dioxo 6-difluoromethyl 17alpha-acetoxy 19-nor pregna 4-ene 3,20-dioxo 6-acetoxymethyl 17alpha-acetoxy 19-nor pregna 4,6-diene 3,20-dioxo 6-methoxymethyl 17alpha-acetoxy 19-nor pregna 4,6-diene 3,20-dioxo 6-hydroxymethyl 17alpha-hydroxy 19-nor pregna 4,6-diene and its acetate in position 17

3,20-dioxo 6-difluoromethyl 17alpha-acetoxy 19-nor pregna 4,6-diene 3,20-dioxo 17alpha-acetoxy 6-chloromethyl 19-nor pregna 4,6-diene 3,20-dioxo 6-tosyloxymethyl 17alpha-acetoxy 19-nor pregna 4,6-diene 3,20-dioxo 6-formyl 17alpha-acetoxy 19-nor pregna 4,6-diene 3,20-dioxo 6-hydroxymethyl 17alpha-methyl 19-nor pregna 4,6-diene 3,20-dioxo 6-ethyl 17alpha-hydroxy 19-nor pregna 4,6-diene and its acetate 3,20-dioxo 6-propyl 17alpha-hydroxy 19-nor pregna 4,6-diene and its acetate The compounds according to the invention show useful pharmacological properties and in particular powerful progestomimetic properties. They can be used, therefore, as a progestational medicament in the treatment or the prevention of syndromes linked with the menopause such as hot flushes, skin problems, circulatory disorders.

To this end, they are used in the form of pharmaceutical compositions intended for administration by parenteral, digestive, rectal, permucous or percutaneous route. They will therefore be presented in the form of injectable solutes or suspensions packaged in vials, self-injectable syringes or multi-dose bottles; in the form of uncoated or coated tablets, sugar-coated pills, capsules, gelules, cachets, powders, rectal suppositories or capsules; solutions or suspensions for percutaneous use in a polar solvent; creams, gels or ointments; and finally, suppositories.

For therapeutic use, the compounds according to the invention are administered at a dose varying from 20 to 50 mg and preferably 5 to 25 mg per unit dose. The daily dose ranges from 5 to 200 mg per day as a function of the therapeutic indication and the administration route.

The invention also relates to a process for producing compounds of formula (A)

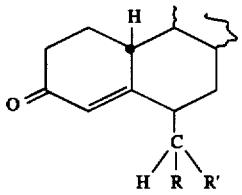

(A)

in which R and R' are defined as previously which Consists of subjecting an enol ether of general formula (II)

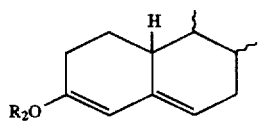

(II)

in which $R_2$ is a lower alkyl radical to the action of a formulation agent of Vislmeier-Hack type in order to form the corresponding 6-formylated derivative (III)

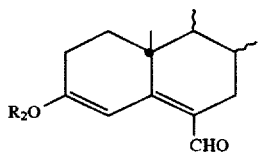

(III)

in which $R_2$ has the previous meaning which can be reduced by the action of a mixed hydride of an alkali metal in order to form the corresponding hydroxy-methylated derivative (IV)

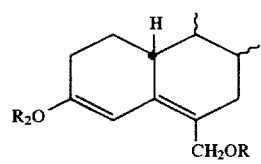

(IV)

in which $R_2$ is defined as previously then this is subjected to an alkylation followed by an acid hydrolysis in order to obtain an alkoxymethylated derivative of formula (V)

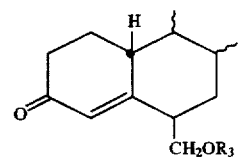

(V)

in which $R_3$ is an optionally substituted lower alkyl radical or to an acylation followed by an acid hydrolysis in order to obtain the acyloxymethylated derivative of general formula (VI)

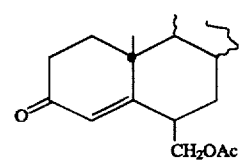

(VI)

in which Ac represents the acyl remainder of an aliphatic, aromatic, heterocyclic organic carboxylic acid or cycloalkyl carboxylic acid having 1 to 10 carbon atoms or to an acylation by a functional derivative of an easily-labile acid, then this is subjected to a mono- or dihalogenation by the action of an alkali metal fluoride in order to form a halogenated derivative of structure

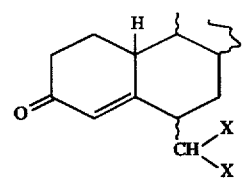

(VII)

or to a dehydration in acid medium in order to obtain a methylidene derivative of formula (VIII)

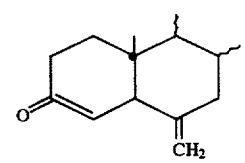

(VIII)

In order to form the compounds for which R' represents hydrogen and R represents a lower alkyl radical the formylated derivative III is reacted with an alkylmetal salt such as an alkyl magnesium halide, an alkyl zinc halide or an alkyl cadmium halide in order to form the corresponding carbinol which is treated in an aqueous acid medium in order to obtain the corresponding alkylidene derivative then isomerized using a noble metal such as palladium into the 6-alkylated derivative.

The invention also relates to a process for obtaining compounds of partial formula B which consists of subjecting an enol ether of partial formula (IV)

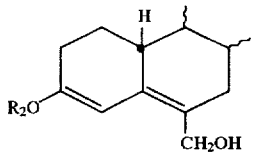
(IV)

in which $R_2$ is a lower alkyl radical to the action of a quinonic dehydrogenation agent in an inert solvent miscible with water in order to form, after destroying the excess reagent, a hydroxy methylated derivative of partial formula (C)

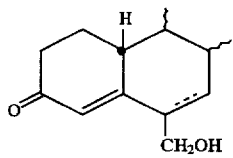
(C)

which can be alkylated by the action of an alkylation agent into the alkyloxy methyl derivative or esterified by the action of a functional derivative of an organic carboxylic acid in order to form an acyloxylated derivative or converted into the halogenated derivative by conversion firstly into the reactive ester of the hydroxy methylated derivative then conversion of this ester into the halogenated derivative by the action of an alkali metal halide in a polar solvent.

In the process according to the invention, the quinonic dehydrogenating agent is preferably dibromodicyanobenzoquinone, chloranil, dichloronaphthoquinone or dichlorodicyanobenzoquinone.

The reactive ester is preferably a methane sulphonate, a paratoluene sulphonate or a trifluoromethyl sulphonate. The alkali metal halide is preferably sodium or potassium fluoride, or sodium chloride in the presence of an alkali metal acetate. The polar solvent is pyridine, dimethylformamide or diethyl acetamide.

The dihalogenomethylated derivatives are obtained by a process which consists of reacting the formylated derivative of partial formula (III) with a dihalogenosulphonium halide such as DAST (diethylaminosulphur trifluoride).

The following examples illustrate the invention without however limiting it.

EXAMPLE I

1 7ALPHA-ACETOXY 3, 20-DIOXO 6-PROPYL 19-NOR 4,6-PREGNADIENE 24 g (57.9 mM) of 17alpha-acetoxy 3-ethoxy 6-formyl 20-oxo 19-nor 3,5-pregnadiene and 240 ml of tetrahydrofuran (THF) are introduced under a nitrogen atmosphere into a flask. Under agitation, 48 ml of a solution of ethylmagnesium chloride in THF titrated at 25% (i.e. 134.4 mM) is added slowly at ambient temperature. Agitation is continued for one hour. 48 ml of 5N aqueous HCl is added while cooling down the medium. The medium is then poured into one litro of water. The product precipitates. It is taken up in methylene chloride and evaporated to dryness. 28 g of residue is obtained which is chromatographed on silica, eluting with a toluene 9.5/ethyl acetate 0.5 mixture. Recrystallization is carried out from methanol and 2.3 g of 17alpha-acetoxy 6-propylidene 3,20-dioxo 19-nor 4-pregnene is obtained.

The above product is introduced into an agitated suspension of 1.5 g of palladiated charcoal with 5% palladium in 220 ml of methanol taken to reflux beforehand. After maintaining the mixture under reflux for 2 hours, it is cooled down and filtered. The product obtained after evaporation to dryness is chromatographed on silica and eluted with a toluene 95/ethyl acetate 5 mixture. 1.6 g of crude product is obtained which is recrystallized from isopropyl ether. 0.9 g of white crystals are separated out. M.p.=161°–162° C.

UV: (acetonitrile) λmax: 285 nm ε=24.218

IR (KBr) carbonyl 1705, 1648 $cm^{-1}$ acetate 1727 $cm^{-1}$ C=C 1614, 1574 $cm^{-1}$

|$^1$H| NMR (CDCl$_3$, 250 MHz)
δ0.70 (s, 3, CH$_3$-18)
0.908 (t, 3, CH$_3$-6-propyl)
2.07 (s, 3, CH$_3$-acetate)
2.11 (s, 3, CH$_3$-2)
6.01 (s, 2, H$_4$ with H$_7$)

EXAMPLE II

17ALPHA-ACETOXY 3,20-DIOXO 6-ETHYL 19-NOR 4,6-PREGNADIENE 5 g (12.07 mM) of 17alpha-acetoxy 3-ethoxy 6-formyl 20-oxo 19-nor 3,5-pregnadiene and 50 ml of tetrahydrofuran (THF) are introduced under a nitrogen atmosphere into a flask. 5 ml of a solution of methylmagnesium chloride in THF titrated at 3mM/ml of magnesium compound is added under agitation and at ambient temperature to the suspension. After one hour, 15 ml of 5N aqueous HCl is added while cooling down the medium, then the mixture is poured into 500 ml of water. The product precipitates. After filtration, washing is carried out with water: 4.5 g, yield: 97%. The product is chromatographed on silica and eluted with a toluene/ethyl acetate mixture (90/10). Recrystallization is carried out from 14 volumes of methanol and 1.5 g of 17alpha-acetoxy 6-ethylidene 3,20-dioxo 19-nor 4-pregnene is separated out.

The above product is added to an agitated suspension of 1.2 g of palladiated charcoal with 5% palladium in 200 ml of methanol taken to reflux beforehand. Reflux is maintained for 45 minutes, the reaction medium is cooled down to ambient temperature, filtered and evaporated to dryness. The residue is chromatographed on silica and eluted with a mixture of toluene and ethyl acetate (90/10). 1 g of product is obtained which is recrystallized from methanol: 0.5 g, creamy white crystals. M.p.=154°–156° C. (Kofler)

Uv: (acetonitrile) λmax: 284 nm ε=22.337

IR (KBr): carbonyls at 1705–1715, 1670 $cm^{-1}$ acetate 1739 $cm^{-1}$ C=C 1614, 1580 $cm^{-1}$

[$^1$H] NMR: (CDCl$_3$ 250 MHz)
δ0.71 (S, 3, CH$_3$-18)
1.08 (t, 3 CH$_3$-6-ethyl)
2.07 (S, 3 CH$_3$-acetate)
2.10 (S, 3 CH$_3$-21)
6.01 (S, 2H, H$_4$ with H$_7$)

EXAMPLE III

17ALPHA-ACETOXY 6-FORMYL 3,20-DIOXO 19-NOR 4,6-PREGNADIENE 2.8 g of 2,3-dichloro 5,6-dicyano p-benzoquinone is introduced under a nitrogen atmosphere and under agitation into a solution of 5 g of 17alpha-acetoxy 3-ethoxy 6-formyl 20-oxo 19-nor 3,5-pregnadiene in 135 ml of acetone and 7.1 ml of water. The temperature rises from 19° to 21° and the reaction medium colours.

After 45 minutes, it is taken up in water and ethyl acetate, washed with N soda then with water until a neutral pH is obtained. After bringing to dryness, the residue is chromatographed on silica and eluted with ethyl acetate. Recrystallization is carried out from ethyl ether hot and cold (−180°). The crystals are washed with ether. 500 mg of creamy white product is obtained, melting at about 190°–200° C.

UV: (acetonitrile) λmax: 272 nm ε=20.000

IR (KBr): carbonyls at 1711, 1688, 1653 cm$^{-1}$ acetates 1733 cm$^{-1}$

|$^1$H| NMR (CDCl$_3$, 250 MHz)
  δ0.70 (S, 3, CH$_3$-18)
  2.00 (S, 3, CH$_3$-acetate)
  2.06 (S, 3, CH$_3$-21)
  7.01 (d, 1) (H$_4$, H$_7$)
  7.12 (d, 1) (H$_4$, H$_7$)
  9.59 (S, 1, aldehyde)

EXAMPLE IV

PREPARATION OF 17ALPHA-ACETOXY 6-HYDROXYMETHYL 3,20-DIOXO 19-NOR 4,6-PREGNADIENE (A) AND 17ALPHA-HYDROXY 6-HYDROXYMETHYL 3,20-DIOXO 19-NOR 4,6-PREGNADIENE (B)

20 g of 17alpha-acetoxy 3-ethoxy 6-hydroxymethyl 20-oxo 19-nor 3,5-pregnadiene, 200 ml (20 vol) of acetone, 40 ml (2 vol) of water and 18.2 g (0.93 p) of 2,3-dichloro 5,6-dicyano p-benzoquinone are introduced under a nitrogen atmosphere into a 2 litre three-necked flask fitted with magnetic stirring.

The reaction is followed by thin layer chromatography. The reaction is complete after 45 minutes. Precipitation is carried out in 1 litre of water. A precipitate is observed which is filtered. The mother liquors are extracted twice with 500 ml of dichloromethane.

The organic phases are washed with water until a neutral pH is obtained. 7.8 g of a brown oil is obtained, yield= 41.9%.

Purification is carried out on a silica column, a first product (A) 5.5 g and a second product (B) 1.2 g are separated out in order.

Product A is recrystallized from methanol and provides 3 g of 17alpha-acetoxy 6-hydroxymethyl 3,20-dioxo 19-nor 4,6-pregnadiene. M.p.=202.4° C.

| NMR: H4 | S 6.37 ppm | 1 proton |
|---|---|---|
| H7 | S 6.01 ppm | 1 proton |
| 6-hydroxymethyl | S 4.34 ppm | 2 protons |
| H C21 | S 2.10 ppm | 3 protons |
| Acetate | S 2.07 ppm | 3 protons |
| H—O | S 1.63 ppm | 1 proton |
| H C18 | S 0.73 ppm | 3 protons |

Product B is also crystallized from methanol and provides 0.3 g of 17alpha-hydroxy 6-hydroxymethyl 3,20-dioxo 4,6-pregnadiene. Melting point (Metler): 251° C.

| NMR: H4 | S 6.38 ppm | 1 proton |
|---|---|---|
| H7 | S 6.01 ppm | 1 proton |
| 6-hydroxymethyl | S 4.33 ppm | 2 protons |
| H C21 | S 2.3 ppm | 3 protons |
| H—O 6 | S 1.63 ppm | 1 proton |
| H C18 | S 0.81 ppm | 3 protons |

EXAMPLE V

PEPARATION OF 17ALPHA-ACETOXY 6-ACETOXYMETHYL 3,20-DIOXO 19-NOR 4, 6-PREGNADIENE 1 g of product A of Example IV, 20 ml of pyridine (20 vol), 2 ml of acetic anhydride (2 vol) are introduced successively into a 100 ml three-necked flask fitted with magnetic stirring and cooling apparatus. The solution is heated at 60° C. for 35 minutes. Precipitation is carried out in a water/ice bath. The product is filtered then purified on a silica column. 0.7 g of a white product is obtained.

| NMR: H4 | S 6.32 ppm | 1 proton |
|---|---|---|
| H7 | S 6.01 ppm | 1 proton |
| 6-acetoxymethyl | S 4.72 ppm | 2 protons (proton of CH2) |
| H C21 | S 211 ppm | 3 protons |
| Me of the acetoxys | S 2.07 ppm | 6 proton (17alpha- and 6-acetoxy) |
| H C18 | S 0.72 ppm | 3 protons |

EXAMPLE VI

PREPARATION OF 17ALPHA-ACETOXY 6-(HYDROXYMETHYL, HEMI-SUCCINATE) 3,20-DIOXO 19-NOR 4,6-PREGNADIENE 1 g of the preceding product (A), 20 ml of prydine (20 vol) and 0.6 g of succinic anhydride are introduced successively into a 100 ml three-necked flask fitted with magnetic stirring and cooling apparatus.

The solution is heated at 60° C. for 4 hours. The excess anhydride is decomposed with water. The product is extracted with toluene and washed with water. The product is purified on a silica column. 0.25 g of a white product is obtained.

| NMR: H4 | S 6.38 ppm | 1 proton |
|---|---|---|
| H7 | S 6.01 ppm | 1 proton |
| 2 methylene protons in position 6 | S 4.75 ppm | 2 protons |
| 4 hemisuccinate protons in position 6 | S 2.66 ppm | 4 protons |
| H C21 | S 2.11 ppm | 3 protons |
| Me 17alpha-acetoxy | S 2.02 ppm | 3 protons |
| H C18 | S 0.72 ppm | 3 protons |

EXAMPLE VII

PREPARATION OF 17BETA-ACETOXY 17ALPHA-ETHYNYL 6-METHYLIDENE 3-OXO 4-ESTRENE 2.8 g of 17beta-acetoxy 3-ethoxy 17alpha-ethynyl 6-formyl 3,5-estradiene, 8.5 ml (abs) ethanol (3.03 vol), 7 ml dimethylformamide (2.5 vol), and 0.13 g sodium borohydride (0.046 p) are introduced under agitation and under a nitrogen atmosphere into a 50 ml three-necked flask. The reaction is stopped after agitation for 22 hours. The reaction medium is hydrolyzed by introducing a solution composed of 2.8 ml (1 vol) of 2N sulphuric acid, 6 ml (2.1 vol) DMF, and 6 ml (2.1 vol) (abs) ethanol over 10 minutes. 2.1 g (yield=84%) of a creamy white product is obtained. M.p.= 157° C.

This compound has already been described in the French Patent Application No. 89.06790 filed on 24th May 1989 in the name of the Applicant.

We claim:
1. A 3-keto-19-nor-pregnene of the formula

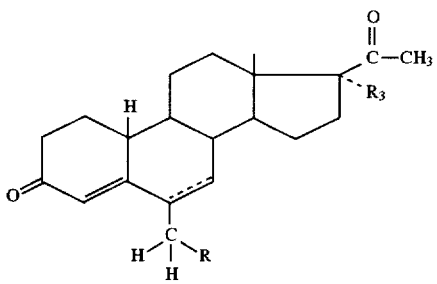

wherein R is selected from the group consisting of —OH and lower acyloxy of an organic carboxylic acid and $R_3$ is selected from the group consisting of methyl, —OH and lower acyloxy of an organic carboxylic acid.

2. A compound of the formula

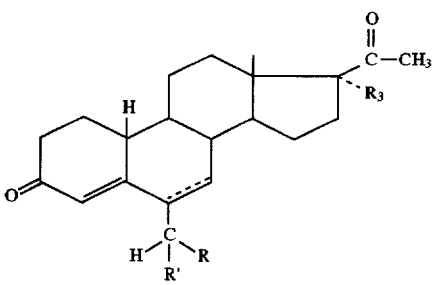

wherein the grouping

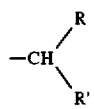

is selected from the group consisting of formyl, hydroxylmethyl, acyloxymethyl, alkoxymethyl and dihalogenomethyl and $R_3$ is selected from the group consisting of methyl, —OH and lower acyloxy of an organic carboxylic acid.

3. A compound selected from the group consisting of:

6-formyl-17α-acetoxy-19-nor-$\Delta^4$-pregnene-3,20-dione, 6-difluoromethyl-17α-acetoxy-19-nor-$\Delta^4$-pregnene-3,20-dione, 6-acetoxymethyl-17α-acetoxy-19-nor-$\Delta^{4,6}$-pregnadiene-3,20-dione, 6-methoxymethyl-17α-acetoxy-19-nor-$\Delta^{4,6}$-pregnadiene-3,20-dione, 6-hydroxymethyl-19-nor-$\Delta^{4,6}$-pregnadiene-17α-ol-3,20-dione and its acetate in position 17, 6-difluoromethyl-17α-acetoxy-19-nor-$\Delta^{4,6}$-pregnadiene-3,20-dione, 6-chloromethyl-17α-acetoxy-19-nor-$\Delta^{4,6}$-pregnadiene-3,20-dione, 6-tosyloxymethyl-17α-acetoxy-19-nor-$\Delta^{4,6}$-pregnadiene-3,20-dione, 6-formyl-17α-acetoxy-19-nor-$\Delta^{4,6}$-pregnadiene 3,20-dione, 6-hydroxymethyl-17α-methyl-19-nor-$\Delta^{4,6}$-pregnadiene-3,20-dione, 6-ethyl-19-nor-$\Delta^{4,6}$-pregnadiene-17α-ol-3,20-dione, 6-propyl-19-nor-$\Delta^{4,6}$-pregnadiene-17α-ol-3,20-dione and its acetate and 6-pivaloyloxymethyl-17α-acetoxy-19-nor-$\Delta^{4,6}$-pregnadiene-17α-ol-3,20-dione.

4. A compound of claim 3 selected from the group consisting of 6-hydroxymethyl-19-nor-$\Delta^{4,6}$-pregnadiene-17α-ol-3,20-dione and its acetate in position 17.

5. A progestomimetic composition comprising a progestomimetically effective amount of a compound of claim 3 and an inert pharmaceutical carrier.

6. A method of treating menopause symptoms in female humans comprising administering to female humans an amount of a compound of claim 3 effective to alleviate the symptoms of menopause.

7. The method of claim 6 wherein the compound is selected from the group consisting of 6-hydroxymethyl-19-nor-$\Delta^{4,6}$-pregnadiene- 17αol-3,20-dione, its 17α-acetoxy derivative and an ester of the 6-hydroxymethyl group.

* * * * *